US008815088B2

(12) United States Patent
Choi et al.

(10) Patent No.: US 8,815,088 B2
(45) Date of Patent: Aug. 26, 2014

(54) DIALYSIS FLUID PUMP, AND HEMODIALYSIS APPARATUS HAVING SAME

(75) Inventors: Nak-Myung Choi, Gyeonggi-do (KR); Kyungsoo Lee, Chungnam (KR); Cho Hay Mun, Seoul (KR); Sa Ram Lee, Gyeonggi-do (JP); Dong Wook Lee, Seoul (KR); Byoung-Goo Min, Gyeonggi-do (KR); Jong-Weon Choi, Seoul (KR)

(73) Assignees: Ancbio Co., Ltd., Gyeonggi-do (KR); Nak-Myung Choi, Gyeonggi-do (KR)

( * ) Notice: Subject to any disclaimer, the term of this patent is extended or adjusted under 35 U.S.C. 154(b) by 184 days.

(21) Appl. No.: 13/580,480

(22) PCT Filed: Jan. 17, 2011

(86) PCT No.: PCT/KR2011/000335
§ 371 (c)(1),
(2), (4) Date: Sep. 5, 2012

(87) PCT Pub. No.: WO2011/105698
PCT Pub. Date: Sep. 1, 2011

(65) Prior Publication Data
US 2013/0008843 A1 Jan. 10, 2013

(30) Foreign Application Priority Data

Feb. 23, 2010 (KR) .................. 10-2010-0016100

(51) Int. Cl.
*A61M 1/16* (2006.01)
*F04B 43/12* (2006.01)
*F04B 9/04* (2006.01)
*F04B 43/08* (2006.01)

(52) U.S. Cl.
CPC .............. *A61M 1/16* (2013.01); *F04B 9/042* (2013.01); *F04B 43/086* (2013.01)
USPC ..... 210/258; 210/236; 210/257.2; 210/416.1; 417/475; 417/476; 417/477.1; 604/6.09; 604/6.11

(58) Field of Classification Search
CPC ........ A61M 1/16; F04B 43/08; F04B 43/082; F04B 43/086; F04B 9/042

USPC ........... 210/236, 257.2, 258, 416.1; 417/475, 417/476, 477.1; 604/6.09, 6.11
See application file for complete search history.

(56) References Cited

U.S. PATENT DOCUMENTS
2011/0139704 A1* 6/2011 Choi et al. ................. 210/416.1

FOREIGN PATENT DOCUMENTS

| JP | 8-334087 A | 12/1996 |
|----|-----------|---------|
| JP | 2008-308994 A | 12/2008 |
| KR | 2004-0026193 A | 3/2004 |
| KR | 2009-0118536 A | 11/2009 |

OTHER PUBLICATIONS
International Search Report: mailed Oct. 19, 2011; PCT/KR2011/000335.

* cited by examiner

*Primary Examiner* — John Kim
(74) *Attorney, Agent, or Firm* — Ladas & Parry LLP (57) ABSTRACT

According to the present invention, a dialysis fluid pump comprises: a housing having an accommodating space formed therein; a dialysis fluid supply tube and a dialysis fluid recovery tube, at least a portion of each of which is accommodated in the accommodating space; a cam rotatably installed in the accommodating space; a motor for rotating the cam; and a first backflow pressure preventer and a second backflow pressure preventer adapted to be mobile in the accommodating space and be pushed by the cam. The dialysis fluid supply tube is made of a flexible material which can be contracted or relaxed, and one end thereof is connected to a dialysis fluid supply tank and the other end thereof is connected to a hemodialysis filter. The dialysis fluid recovery tube is made of a flexible material which can be contracted or relaxed, and one end thereof is connected to a dialysis fluid recovery tank and the other end thereof connected to the hemodialysis filter. The cam has a cam surface for pressing the dialysis fluid supply tube and recovery tube to discharge the dialysis fluid from the inside of the dialyzing fluid supply tube and of the dialyzing fluid recovery tube. The first backflow pressure preventer and the second backflow pressure preventer prevent the dialysis fluid from flowing backward through the dialysis fluid supply tube and the dialysis fluid recovery tube.

7 Claims, 9 Drawing Sheets

DIALYSIS FLUID PUMP, AND HEMODIALYSIS APPARATUS HAVING SAME

TECHNICAL FIELD

The present invention relates to a hemodialysis apparatus for filtering impurities contained in blood by moving blood and dialysis fluid with a hemodialysis filter interposed therebetween, and more particularly to a dialysis fluid pump and a hemodialysis apparatus having the same for supplying dialysis fluid to the hemodialysis filter.

BACKGROUND ART

When the kidney shows partial or overall dysfunction, waste matter that would otherwise be discharged as urine from the body is accumulated in blood, and moreover electrolyte imbalance in the body occurs. As a method for correcting such kidney failure, extracorporeal circulation using a hemodialysis apparatus has been widely performed. Extracorporeal circulation using a hemodialysis apparatus is a method that removes waste matter contained in blood from the body using the principle of diffusion or filtering, and also achieves electrolyte balance.

Typically, a hemodialysis apparatus is configured to outwardly discharge impurities contained in blood using a hemodialysis filter that is equipped with a dialysis membrane within a single housing to enable mass transfer through the dialysis membrane between blood and dialysis fluid. There are two kinds of hemodialysis filters including a hollow fiber membrane type hemodialysis filter and a flat sheet membrane type hemodialysis filter based on the kind of the dialysis membrane.

Among these, the hollow fiber membrane type hemodialysis filter, which is formed by loading a bundle of hollow fiber membranes into a cylindrical container, attaching resin layers to both ends of the bundle, and forming ports through the resin layers, is preferred. This is because the hollow fiber membrane type hemodialysis filter has a large contact area with blood or dialysis fluid despite a small capacity thereof, thus providing superior mass transfer efficiency.

A conventional hemodialysis apparatus includes a hemodialysis filter, a dialysis fluid supply tank for supplying clean dialysis fluid to the hemodialysis filter, a dialysis fluid recovery tank for storing dialysis fluid having passed through the hemodialysis filter, a blood pump for supplying blood to the hemodialysis filter, and a dialysis fluid pump for supplying the dialysis fluid stored in the dialysis fluid supply tank to the hemodialysis filter. The hemodialysis filter is provided with a blood inlet for inflow of blood, a blood outlet for outflow of blood, a dialysis fluid inlet for inflow of dialysis fluid, and a dialysis fluid outlet for outflow of dialysis fluid. Blood and dialysis fluid move in opposite directions within the hemodialysis filter.

Since the blood pump is located toward the blood inlet and the dialysis fluid pump is located toward the dialysis fluid inlet, blood is reduced in pressure with decreasing distance toward the blood outlet, and dialysis fluid is reduced in pressure with decreasing distance toward the dialysis fluid outlet. Diffusion of moisture, electrolyte and waste matter, for example, from blood to dialysis fluid occurs in a region where the pressure of blood is greater than the pressure of dialysis fluid, and dialysis fluid is transferred to blood in a region where the pressure of dialysis fluid is greater than the pressure of blood.

DISCLOSURE

Technical Problem

To enhance hemodialysis efficiency of a hemodialysis apparatus, it is necessary to extend time that causes a pressure difference between blood and dialysis fluid, or to lengthen a path where blood and dialysis fluid meet each other. However, lengthening the path where blood and dialysis fluid meet each other requires an increased size of a hemodialysis filter and consumption of a greater amount of dialysis membranes.

The present invention is devised to solve the above described problems, and it is an object of the present invention to provide a dialysis fluid pump and a hemodialysis apparatus having the same, which are capable of improving hemodialysis efficiency without requiring an increase in the size of a hemodialysis filter.

Technical Solution

To achieve the above described object, in accordance with one embodiment of the present invention, a dialysis fluid pump includes a housing having an accommodating space therein, a dialysis fluid supply tube and a dialysis fluid recovery tube, at least a portion of each of which is accommodated in the accommodating space, a cam rotatably installed in the accommodating space, a motor for rotating the cam, and a first backflow pressure preventer and a second backflow pressure preventer movably installed in the accommodating space so as to be pushed by the cam. The dialysis fluid supply tube is formed of a flexible material that can be contracted and relaxed, and one end of the dialysis fluid supply tube is connected to the dialysis fluid supply tank and the other end is connected to the hemodialysis filter. The dialysis fluid recovery tube is formed of a flexible material that can be contracted and relaxed, and one end of the dialysis fluid recovery tube is connected to the dialysis fluid recovery tank and the other end is connected to the hemodialysis filter. The cam has a cam surface for pressing the dialysis fluid supply tube and the dialysis fluid recovery tube to discharge the dialysis fluid from the inside of the dialysis fluid supply tube and of the dialysis fluid recovery tube, respectively. The first backflow pressure preventer includes a first pressure protrusion adapted to contract a first portion of the dialysis fluid supply tube and a second pressure protrusion adapted to contract a first portion of the dialysis fluid recovery tub. The second backflow pressure preventer includes a third pressure protrusion adapted to contract a second portion of the dialysis fluid supply tube and a fourth pressure protrusion adapted to contract a second portion of the dialysis fluid recovery tube.

The dialysis fluid pump may according to the embodiment of the present invention further include a first pumping pressure member movably installed in the accommodating space so as to be pushed by the cam, wherein the first pumping pressure member includes a pressure surface adapted to press a third portion between the first portion and the second portion of the dialysis fluid supply tube so as to discharge the dialysis fluid from the inside of the dialysis fluid supply tube, and a second pumping pressure member movably installed in the accommodating space so as to be pushed by the cam, wherein the second pumping pressure member includes a pressure surface adapted to press a third portion between the first portion and the second portion of the dialysis fluid recovery tube so as to discharge the dialysis fluid from the inside of the dialysis fluid recovery tube.

The dialysis fluid pump according to the embodiment of the present invention may further include elastic members connected respectively to the first pumping pressure member, the second pumping pressure member, the first backflow pressure preventer and the second backflow pressure preventer, to elastically push the first pumping pressure member, the second pumping pressure member, the first backflow pressure preventer and the second backflow pressure preventer toward the cam.

The dialysis fluid pump according to the embodiment of the present invention may further include first guide means for coupling the first pumping pressure member to the housing in a sliding manner, to guide linear movement of the first pumping pressure member, second guide means for coupling the second pumping pressure member to the housing in a sliding manner, to guide linear movement of the second pumping pressure member, third guide means for coupling the first backflow pressure preventer to the housing in a sliding manner, to guide linear movement of the first backflow pressure preventer, and fourth guide means for coupling the second backflow pressure preventer to the housing in a sliding manner, to guide linear movement of the second backflow pressure preventer.

The first pumping pressure member, the second pumping pressure member, the first backflow pressure preventer, and the second backflow pressure preventer may be arranged at an interval of 90 degrees around the cam, such that the first pumping pressure member and the second pumping pressure member face each other with the cam interposed therebetween and the first backflow pressure preventer and the second backflow pressure preventer face each other with the cam interposed therebetween.

A plurality of contact rollers may be rotatably coupled respectively to distal ends of the first pumping pressure member, the second pumping pressure member, the first backflow pressure preventer, and the second backflow pressure preventer, so as to come into contact with the cam surface.

In accordance with another embodiment of the present invention, a hemodialysis apparatus includes a hemodialysis filter to permit passage of blood and dialysis fluid therethrough, the hemodialysis filter having a dialysis membrane adapted to enable mass transfer between the blood and the dialysis fluid, a blood pump for pumping the blood to the hemodialysis filter, a dialysis fluid supply tank for storing clean dialysis fluid, a dialysis fluid recovery tank for recovering the dialysis fluid having passed through the hemodialysis filter, and a dialysis fluid pump for pumping dialysis fluid from the dialysis fluid supply tank to the hemodialysis filter and in turn from the hemodialysis filter to the dialysis fluid recovery tank. The dialysis fluid pump includes a housing having an accommodating space therein, a dialysis fluid supply tube and a dialysis fluid recovery tube, at least a portion of each of which is accommodated in the accommodating space, a cam rotatably installed in the accommodating space, a motor for rotating the cam, and a first backflow pressure preventer and a second backflow pressure preventer movably installed in the accommodating space so as to be pushed by the cam.

Advantageous Effects

A dialysis fluid pump and a hemodialysis apparatus having the same according to the present invention can increase the magnitude of a pressure difference between blood and dialysis fluid and the frequency of the occurrence of the pressure difference by generating pulsating flow of dialysis fluid to be supplied to a hemodialysis filter. This has the effect of enhancing hemodialysis efficiency.

DESCRIPTION OF REFERENCE NUMERALS

100: Hemodialysis apparatus
110: hemodialysis filter
118: blood pump 120: dialysis fluid supply tank
122: dialysis fluid recovery tank 124: balancer
130: dialysis fluid pump 131: housing
132: dialysis fluid supply tube
133: dialysis fluid recovery tube
134: first pumping pressure member
135: second pumping pressure member
136: first backflow pressure preventer
137: second backflow pressure preventer
138: cam 139: motor
146, 147, 148, 149: guide groove 155: cam surface
159, 167: pressure portion
161, 169, 177, 185: contact roller
163, 170, 177, 186: spring
175, 176, 183, 184: first, second, third and fourth pressure protrusions

BEST MODE

Hereinafter, a dialysis fluid pump and a hemodialysis apparatus having the same according to an embodiment of the present invention will be described in detail with reference to the accompanying drawings.

In the following description of the present invention, the size, shape or the like of constituent elements illustrated in the drawings may be exaggerated or schematically illustrated for clarity and convenience of explanation. Also, the terms particularly defined taking into consideration the configurations and operations of the present invention may be changed based on intentions of users or operators and customs. These terms should be constructed as meanings and concepts conforming to the technical sprit of the present invention based on the general context of this specification.

Figure 1:
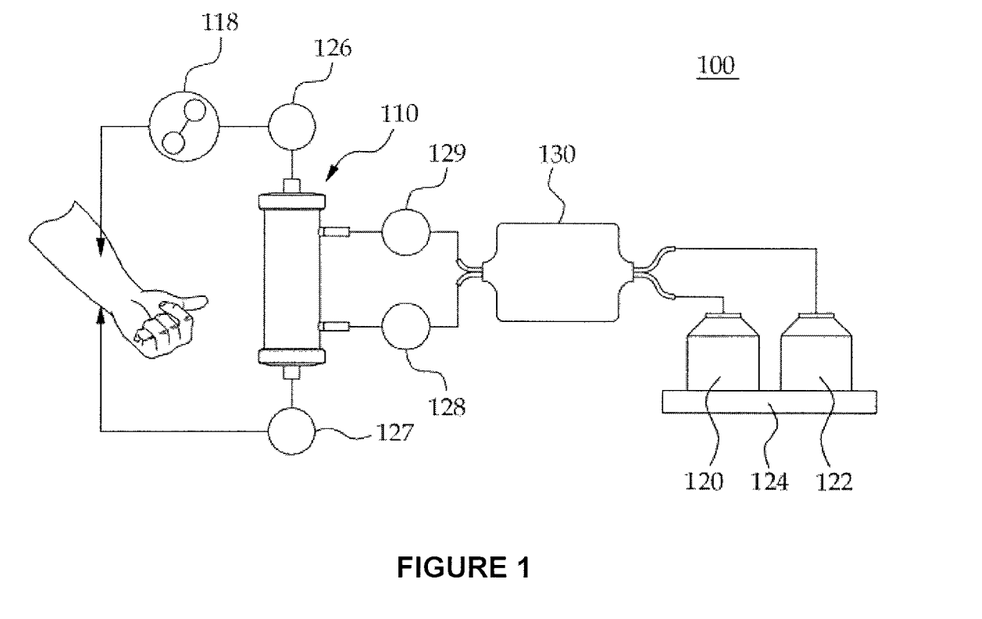
FIG. 1 is a diagram view schematically illustrating a configuration of a hemodialysis apparatus according to an embodiment of the present invention.

As illustrated in FIG. 1, the hemodialysis apparatus 100 according to the embodiment of the present invention includes a hemodialysis filter 110 configured to permit passage of both blood and dialysis fluid therethrough, the hemodialysis filter 110 serving to discharge impurities contained in blood along with dialysis fluid, a blood pump 118 for pumping blood of a patient to the hemodialysis filter 110, a dialysis fluid supply tank 120 for storing clean dialysis fluid therein, a dialysis fluid recovery tank 122 for storing dialysis fluid having passed through the hemodialysis filter 110 therein, and a dialysis fluid pump 130 for supplying dialysis fluid to the hemodialysis filter 110 and recovering dialysis fluid of the hemodialysis filter 110.

The hemodialysis filter 100, the blood pump 118, and the dialysis fluid pump 130 are connected to one another via connection pipes. Pressure gauges 126, 127, 128 and 129 for measuring the pressure of blood or dialysis fluid may be coupled respectively to specific portions of the connection pipes from which blood is introduced into the hemodialysis filter 110 or into which dialysis fluid from the hemodialysis filter 110 is discharged. In the hemodialysis apparatus 100 as described above, as mass transfer between the blood and the dialysis fluid occurs within the hemodialysis filter 110, impurities contained in the blood can be discharged outward.

Figure 2:
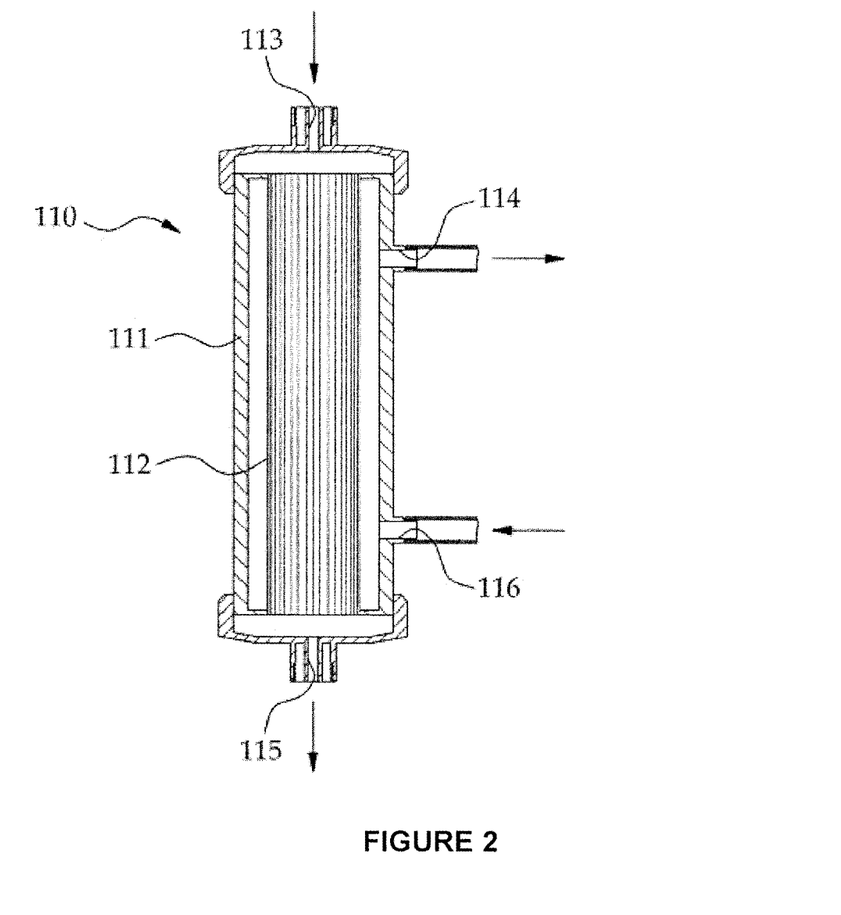
FIG. 2 is a sectional view illustrating a hemodialysis filter of the hemodialysis apparatus according to the embodiment of the present invention.

As illustrated in FIG. 2, the hemodialysis filter 110 includes a container 111 having an interior space and a dialysis membrane 112 accommodated in the interior space of the container 111. The container 111 is provided at and near an upper end thereof with a blood inlet 113 for inflow of blood and a dialysis fluid outlet 114 for outflow of dialysis fluid. Also, the container 111 is provided at and near a lower end thereof with a blood outlet 115 for outflow of blood and a dialysis fluid inlet 116 for inflow of dialysis fluid. As such, the blood flows from top to bottom and the dialysis fluid flows from bottom to top within the container 111. Within the hemodialysis filter 110, diffusion of moisture, electrolyte and waste matter from the blood to the dialysis fluid occurs in a region where the pressure of blood is greater than the pressure of dialysis fluid, and the dialysis fluid is transferred to the blood in a region where the pressure of dialysis fluid is greater than the pressure of blood.

The flow of blood is accomplished by the blood pump 118, and the supply and recovery of dialysis fluid are accomplished by the dialysis fluid pump 130 and a balancer 124. The balancer 124 controls the dialysis fluid pump 130 by comparing clean dialysis fluid to be supplied to the hemodialysis filter 110 with dialysis fluid recovered from the hemodialysis filter 110, thereby serving to regulate supply of dialysis fluid and recovery of dialysis fluid.

Figure 3:
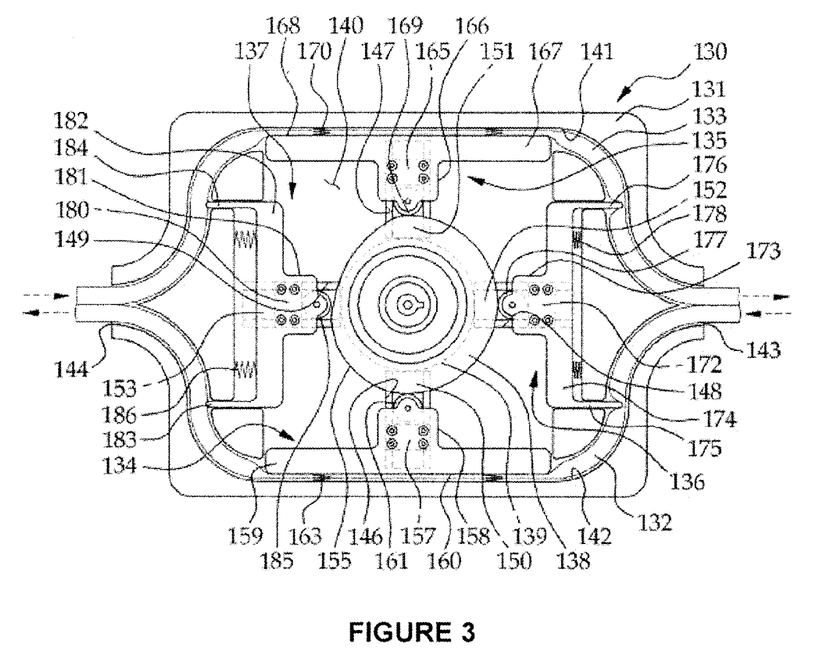
FIG. 3 is a view illustrating a dialysis fluid pump of the hemodialysis apparatus according to the embodiment of the present invention.

As illustrated in FIG. 3, the dialysis fluid pump 130 includes a housing 131, a dialysis fluid supply tube 132 and a dialysis fluid recovery tube 133, at least a portion of each of which is accommodated in the housing 131, a first pumping pressure member 134 for pumping the dialysis fluid from the dialysis fluid supply tube 132 to the hemodialysis filter 110, a second pumping pressure member 135 for pumping the dialysis fluid from the dialysis fluid recovery tube 133 to the dialysis fluid recovery tank 122, a first backflow pressure preventer 136 and a second backflow pressure preventer 137 for preventing backflow of dialysis fluid that flows through the dialysis fluid supply tube 132 and the dialysis fluid recovery tube 133, a cam 138 rotatably installed in the housing 131, and a motor 139 for rotating the cam 138.

The housing 131 has an accommodating space 140. The accommodating space 140 contains a dialysis fluid supply tube accommodating recess 142 for accommodating the dialysis fluid supply tube 132 and a dialysis fluid accommodating recess 141 for accommodating the dialysis fluid recovery tube 133. The housing 131 is provided at left and right distal ends thereof with a first connection hole 143 and a second connection hole 144 for communicating the accommodating space 140 with the outside. Four guide grooves 146, 147, 148 and 149 are linearly indented in an inner surface of the housing 131. The guide grooves 146, 147, 148 and 149 are arranged at an interval of 90 degrees, such that the two guide grooves 148 and 149 are located on the same axis as the first connection hole 143 and the second connection hole 144 and the other two guide grooves 146 and 147 are located on the same axis perpendicular to the guide grooves 148 and 149. Linear guide rails 150, 151, 152 and 153 are respectively seated in the guide grooves 146, 147, 148 and 149.

The cam 138 is rotatably installed approximately at the center of the accommodating space 140. The cam 138 is provided at an outer perimeter thereof with a cam surface 155 for pressing the first pumping pressure member 134, the second pumping pressure member 135, the first backflow pressure preventer 136 and the second backflow pressure preventer 137. The motor 139 for rotating the cam 138 may be coupled to the housing 131, or may be mounted at the outside of the housing 131 so as to be connected to the cam 138.

The dialysis fluid supply tube 132 is formed of a flexible material that can be contracted or relaxed. A portion of the dialysis fluid supply tube 132 is accommodated in the dialysis fluid supply tube accommodating recess 142 contained in the receiving space 140. One end of the dialysis fluid supply tube 132 is connected to the dialysis fluid supply tank 120 through the first connection hole 143, and the other end of the dialysis fluid supply tube 132 is connected to the hemodialysis filter 110 through the second connection hole 144.

When the first pumping pressure member 134 applies pressure to the dialysis fluid supply tube 132, the dialysis fluid supply tube 132 is pressed, causing discharge of the dialysis fluid from the inside of the dialysis fluid supply tube 132 to the hemodialysis filter 110. Once the pressure applied by the first pumping pressure member 134 is removed, the dialysis fluid supply tube 132 is elastically restored to an original state. While the dialysis fluid supply tube 132 expands to an original state thereof, the dialysis fluid stored in the dialysis fluid supply tank 120 is suctioned into the dialysis fluid supply tube 132. The dialysis fluid supply tube 132 may be formed of various materials, such as rubber, silicone and resin, for example, that can be contracted upon receiving pressure, and then can be elastically restored to an original state thereof upon removal of the pressure.

The dialysis fluid recovery tube 133 is formed of a flexible material that can be contracted or relaxed, similar to the dialysis fluid supply tube 132. A portion of the dialysis fluid recovery tube 133 is accommodated in the dialysis fluid recovery tube accommodating recess 141 contained in the receiving space 140. One end of the dialysis fluid recovery tube 133 is connected to the dialysis fluid recovery tank 122 through the first connection hole 143, and the other end of the dialysis fluid recovery tube 133 is connected to the hemodialysis filter 110 through the second connection hole 144.

When the second pumping pressure member 135 applies pressure to the dialysis fluid recovery tube 133, the dialysis fluid recovery tube 133 is pressed, causing discharge of the dialysis fluid from the inside of the dialysis fluid recovery tube 133 to the dialysis fluid recovery tank 122. Once the pressure applied by the second pumping pressure member 135 is removed, the dialysis fluid recovery tube 133 is elastically restored to an original state. While the dialysis fluid recovery tube 133 expands to an original state thereof, the dialysis fluid stored in the hemodialysis filter 110 is suctioned into the dialysis fluid recovery tube 133.

As illustrated in FIG. 3, the first pumping pressure member 134 serves to enable discharge of the dialysis fluid from the inside of the dialysis fluid supply tube 132 to the hemodialysis filter 110, and is fitted into the guide groove 146 of the housing 131 in a sliding manner. The first pumping pressure member 134 includes a sliding portion 158 having a slider 157 that is coupled to the guide rail 150 inside the guide groove 146 in a sliding manner, and a pressure portion 159 connected to the sliding portion 158 so as to apply pressure to the dialysis fluid supply tube 132 accommodated in the accommodating space 140. The pressure portion 159 is provided at a distal end thereof with a pressure surface 160 that comes into contact with the dialysis fluid supply tube 132.

The guide rail 150 and the slider 157 constitute first guide means for coupling the first pumping pressure member 134 to the housing 131 in a sliding manner. Instead of the illustrated configuration, the first guide means may be replaced by other structures capable of guiding linear movement of the first pumping pressure member 134, such as linear elongated grooves or rails, for example.

To enhance the supply efficiency of the dialysis fluid, it is necessary to increase the discharge unit of the dialysis fluid by increasing the press area of the dialysis fluid supply tube 132. To this end, the pressure portion 159 has a possible maximum size under conditions of not interfering with the remaining region of the accommodating space 140, and it is desirable to increase the size of the dialysis fluid supply tube 132 that is pressed by the pressure portion 159. The pressure surface 160 may advantageously be a flat surface or a concavely curved surface in terms of increase in the press magnitude of the dialysis fluid supply tube 132. The pressure portion 159 may have a curvilinear contour other than a linear contour as illustrated. In this case, a portion of the dialysis fluid supply tube 132 that comes into contact with the pressure portion 159 must have a curvilinear contour corresponding to that of the pressure portion 159.

A contact roller 161 is provided at a distal end of the sliding portion 158 of the first pumping pressure member 134 so as to come into contact with the cam surface 155. The contact roller 161 is rotatably coupled to the sliding portion 158. The contact roller 161 is rotated when coming into contact with the cam surface 155. This reduces friction with the cam 138, thereby preventing wear of the first pumping pressure member 134 or the cam 138. Of course, the contact roller 161 may be omitted, and the cam 138 may come into direct contact with the first pumping pressure member 134. When the cam surface 155 applies pressure to the contact roller 161, the first pumping pressure member 134 slides toward the dialysis fluid supply tube 132, thereby applying pressure to the dialysis fluid supply tube 132.

The first pumping pressure member 134 is elastically forced away from the dialysis fluid supply tube 132 by a plurality of springs 163. Once pressure is removed by the cam 138, the first pumping pressure member 134 is moved to an original position thereof by elasticity of the dialysis fluid supply tube 132 and elasticity of the plurality of springs 163. The springs 163 assist the first pumping pressure member 134 in returning to an original position thereof, enabling more rapid elastic restoration of the dialysis fluid supply tube 132. Of course, the springs 163 may be omitted. In this case, the dialysis fluid supply tube 132 may expand to an original state thereof by elastically pushing the first pumping pressure member 134.

The second pumping pressure member 135 serves to enable discharge of the dialysis fluid from the inside of the dialysis fluid recovery tube 133 to the dialysis fluid recovery tank 122, and is fitted into the guide groove 147 of the housing 131 in a sliding manner. The first pumping pressure member 134 includes a sliding portion 166 having a slider 165 that is coupled to the guide rail 151 inside the guide groove 147 in a sliding manner, and a pressure portion 167 connected to the sliding portion 166 so as to apply pressure to the dialysis fluid recovery tube 133 accommodated in the accommodating space 140.

The guide rail 151 and the slider 165 constitute second guide means for coupling the second pumping pressure member 135 to the housing 131 in a sliding manner. Instead of the illustrated configuration, the second guide means may be replaced by other structures capable of guiding linear movement of the second pumping pressure member 135, such as linear elongated grooves or rails, for example.

A pressure surface 168 is provided at a distal end of the pressure portion 167 that comes into contact with the dialysis fluid supply tube 132. A contact roller 169 is rotatably coupled to a distal end of the sliding portion 166 so as to come into contact with the cam surface 155. The second pumping pressure member 135 is elastically forced toward the cam 138 by a plurality of springs 170. A detailed configuration of the second pumping pressure member 135 is equal to that of the above described first pumping pressure member 134, and thus a detailed description thereof will be omitted hereinafter.

As illustrated in FIG. 3, the first backflow pressure preventer 136 serves not only to prevent the dialysis fluid from flowing backward from the dialysis fluid supply tube 132 to the dialysis fluid supply tank 120, but also to prevent the dialysis fluid recovered to the dialysis fluid recovery tank 122 from flowing backward to the dialysis fluid recovery tube 133. The first backflow pressure preventer 136 is fitted into the guide groove 148 of the housing 131 in a sliding manner.

The first backflow pressure preventer 136 includes a sliding portion 173 having a slider 172 that is coupled to the guide rail 152 in the guide groove 148 in a sliding manner, a connecting portion 174 connected to the sliding portion 173, a first pressure protrusion 175 connected to one end of the connecting portion 174 so as to assist contraction of a first portion (P1, see FIG. 5) of the dialysis fluid supply tube 132 accommodated in the accommodating space 140, and a second pressure protrusion 176 connected to the other end of the connecting portion 174 to assist contraction of a first portion (P4, see FIG. 5) of the dialysis fluid recovery tube 133 accommodated in the accommodating space 140.

The guide rail 152 and the slider 172 constitute third guide means for coupling the first backflow pressure preventer 136 to the housing 131 in a sliding manner. Instead of the illustrated configuration, the third guide means may be replaced by other structures capable of guiding linear movement of the first backflow pressure preventer 136, such as linear elongated grooves or rails, for example.

The first pressure protrusion 175 serves to assist contraction of the first portion P1 of the dialysis fluid supply tube 132, and consequently contraction of an inner flow path of the dialysis fluid supply tube 132, thereby restricting the flow of dialysis fluid through the dialysis fluid supply tube 132. That is, the first pressure protrusion 175 serves to prevent the dialysis fluid from flowing backward from the dialysis fluid supply tube 132 to the dialysis fluid supply tank 120. It is desirable that a distal end of the first pressure protrusion 175 be as thin as possible to ensure rapid contraction of the inner flow path of the dialysis fluid supply tube 132, but have a thickness not causing damage to an outer surface of the dialysis fluid supply tube 132.

The second pressure protrusion 176 serves to assist contraction of the first portion P4 of the dialysis fluid recovery tube 133, and consequently, contraction of an inner flow path of the dialysis fluid recovery tube 133, thereby restricting the flow of dialysis fluid through the dialysis fluid recovery tube 133. That is, the second pressure protrusion 176 serves to prevent the dialysis fluid from flowing backward from the dialysis fluid supply tank 122 to the dialysis fluid recovery tube 133. It is desirable that a distal end of the second pressure protrusion 176 be as thin as possible to ensure rapid contraction of the inner flow path of the dialysis fluid recovery tube 133, but have a thickness not causing damage to an outer surface of the dialysis fluid recovery tube 133.

A contact roller 177 is provided at a distal end of the sliding portion 173 of the first backflow pressure preventer 136 so as to come into contact with the cam surface 155. The contact roller 177 is rotatably coupled to the sliding portion 173. The contact roller 177 is rotated when coming into contact with the cam surface 155. This reduces friction with the cam 138, thereby preventing wear of the first backflow pressure preventer 136 or the cam 138. Of course, the contact roller 177 may be omitted, and the cam 138 may come into direct contact with the first backflow pressure preventer 136.

The first backflow pressure preventer 136 is elastically forced toward the cam 138 by a plurality of springs 178. Once pressure is removed by the cam 138, the first backflow pressure preventer 136 is moved to an original position thereof by elasticity of the dialysis fluid supply tube 132, elasticity of the dialysis fluid recovery tube 133 and elasticity of the plurality of springs 178.

The springs 178 assist the first backflow pressure preventer 136 in returning to an original position thereof, enabling more rapid elastic restoration of the dialysis fluid supply tube 132 and the dialysis fluid recovery tube 133. Of course, the springs 178 may be omitted. In this case, the dialysis fluid supply tube 132 and the dialysis fluid recovery tube 133 may expand to an original state thereof by elastically pushing the first backflow pressure preventer 136.

The second backflow pressure preventer 137 serves not only to prevent the dialysis fluid supplied to the hemodialysis filter 110 from flowing backward to the dialysis fluid supply tube 132, but also to prevent the dialysis fluid from flowing backward from the dialysis fluid recovery tube 133 to the hemodialysis filter 110. The second backflow pressure preventer 137 is fitted into the guide groove 149 of the housing 131 in a sliding manner.

The second backflow pressure preventer 137 includes a sliding portion 181 having a slider 180 that is coupled to the guide rail 153 in the guide groove 149 in a sliding manner, a connecting portion 182 connected to the sliding portion 181, a third pressure protrusion 183 connected to one end of the connecting portion 182 so as to assist contraction of a second portion (P2, see FIG. 5) of the dialysis fluid supply tube 132 accommodated in the accommodating space 140, and a fourth pressure protrusion 184 connected to the other end of the connecting portion 182 to assist contraction of a second portion (P5, see FIG. 5) of the dialysis fluid recovery tube 133 accommodated in the accommodating space 140.

The guide rail 153 and the slider 180 constitute fourth guide means for coupling the second backflow pressure preventer 137 to the housing 131 in a sliding manner. Instead of the illustrated configuration, the fourth guide means may be replaced by other structures capable of guiding linear movement of the second backflow pressure preventer 137, such as linear elongated grooves or rails, for example.

A contact roller 185 is rotatably coupled to a distal end of the sliding portion 181 so as to come into contact with the cam surface 155. A plurality of springs 186 is coupled to the connecting portion 182 so as to elastically push the second backflow pressure preventer 137 toward the cam 138. A detailed configuration of the second pumping pressure member 135 is equal to that of the above described first pumping pressure member 134, and thus a detailed description thereof will be omitted hereinafter.

The third pressure protrusion 183 serves to assist contraction of the second portion P2 of the dialysis fluid supply tube 132, and consequently contraction of an inner flow path of the dialysis fluid supply tube 132, thereby restricting the flow of dialysis fluid through the dialysis fluid supply tube 132. That is, the third pressure protrusion 183 serves to prevent the dialysis fluid supplied to the hemodialysis filter 110 from flowing backward to the dialysis fluid supply tube 132.

The fourth pressure protrusion 184 serves to assist contraction of the second portion P5 of the dialysis fluid recovery tube 133, and consequently contraction of an inner flow path of the dialysis fluid recovery tube 133, thereby restricting the flow of dialysis fluid through the dialysis fluid recovery tube 133. That is, the fourth pressure protrusion serves to prevent the dialysis fluid from flowing backward from the dialysis fluid recovery tube 133 to the hemodialysis filter 110.

Figure 4:
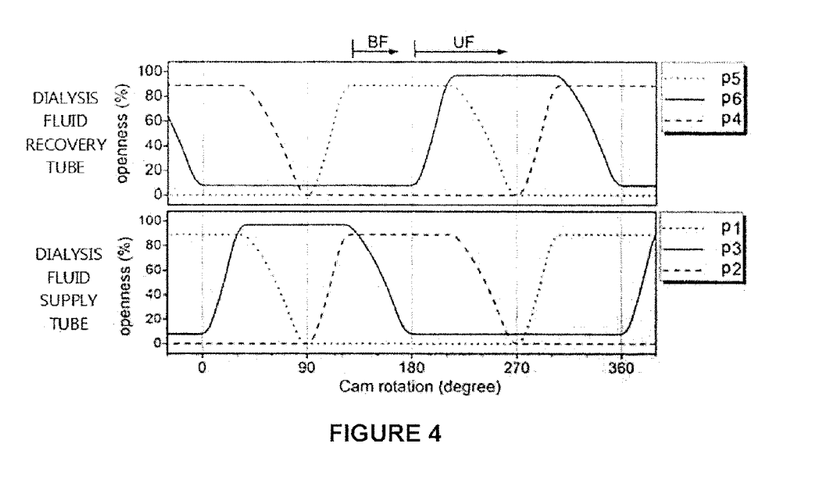
FIG. 4 is a graph illustrating openness of each portion of a dialysis fluid supply tube and a dialysis fluid recovery tube included in the dialysis fluid pump illustrated in FIG. 3.

FIG. 4 illustrates openness of each portion of the dialysis fluid supply tube 132 and the dialysis fluid recovery tube 133 accommodated in the accommodating space 140. The openness refers to a ratio of an original inner diameter of each tube 132 or 133 to an inner diameter of the pressed tube 132 or 133. Considering the openness of each portion of the dialysis fluid supply tube 132, the openness of a middle portion P3 that is pressed by the first pumping pressure member 134 is within a range of 8% to 96% based on rotation of the cam 138. Also, the openness of the first portion P1 and the second portion P2 is within a range of 0% to 88% based on rotation of the cam 138. In the supply order of the dialysis fluid, the first portion P1, the middle portion P3 and the second portion P2 respectively function as the atrioventricular valve, the left ventricle and the aortic valve of the human body.

Considering the openness of each portion of the dialysis fluid recovery tube 133, the openness of a middle portion P6 that is pressed by the second pumping pressure member 135 is within a range of 8% to 96% based on rotation of the cam 138. Also, the openness of the first portion P4 and the second portion P5 is within a range of 0% to 88% based on rotation of the cam 138. In the recovery order of the dialysis fluid, the second portion P5, the middle portion P6 and the first portion P4 respectively function to correspond to the first portion P1, the middle portion P3 and the second portion P2 of the dialysis fluid supply tube 132. In this case, each phase difference is 180 degrees.

Hereinafter, operation of the dialysis fluid pump 130 according to the embodiment of the present invention will be described with reference to the accompanying drawings.

Figure 5:
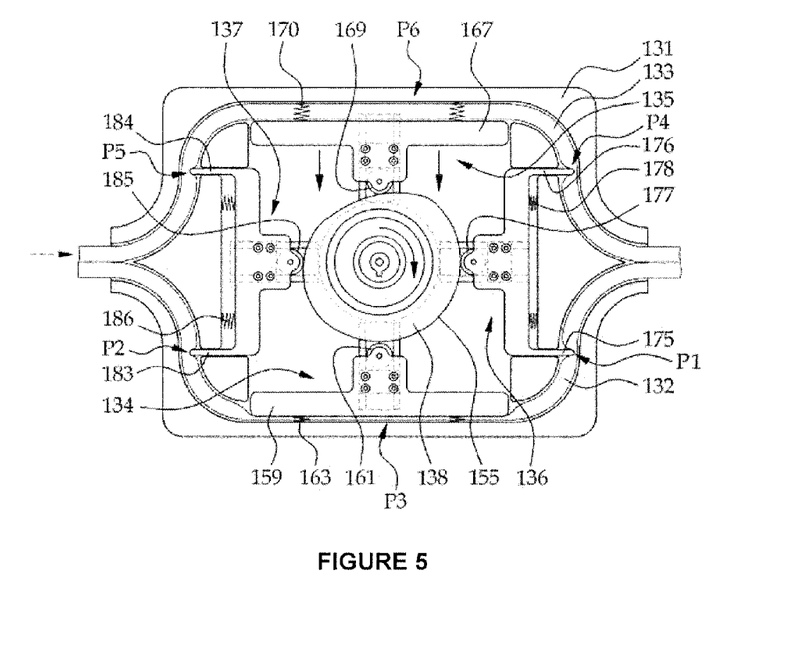
FIGS. 5 to 8 are explanatory views illustrating operation of the dialysis fluid pump illustrated in FIG. 3.

As illustrated in FIG. 5, if pressure applied to the second pumping pressure member 135 is removed in a state in which the cam surface 155 applies pressure to the first backflow pressure preventer 136 via rotation of the cam 138, external force is applied to the second pumping pressure member 135 to move the second pumping pressure member 135 toward the cam 138. In this case, as the second pumping pressure member 135 is pushed toward the cam 138 by elasticity of the springs 170 and the dialysis fluid recovery tube 133, the dialysis fluid recovery tube 133 expands to an original state thereof.

Once the dialysis fluid recovery tube 133 has expanded, the dialysis fluid is suctioned from the hemodialysis filter 110 to the dialysis fluid recovery tube 133. In this case, since the second protrusion 176 of the first backflow pressure preventer 136 presses the first portion P4 of the dialysis fluid recovery tube 133 and restricts the flow of dialysis fluid with respect to the dialysis fluid recovery tank 122, there occurs no suction of the recovered dialysis from the dialysis fluid recovery tank 122 into the dialysis fluid recovery tube 133.

Figure 6:
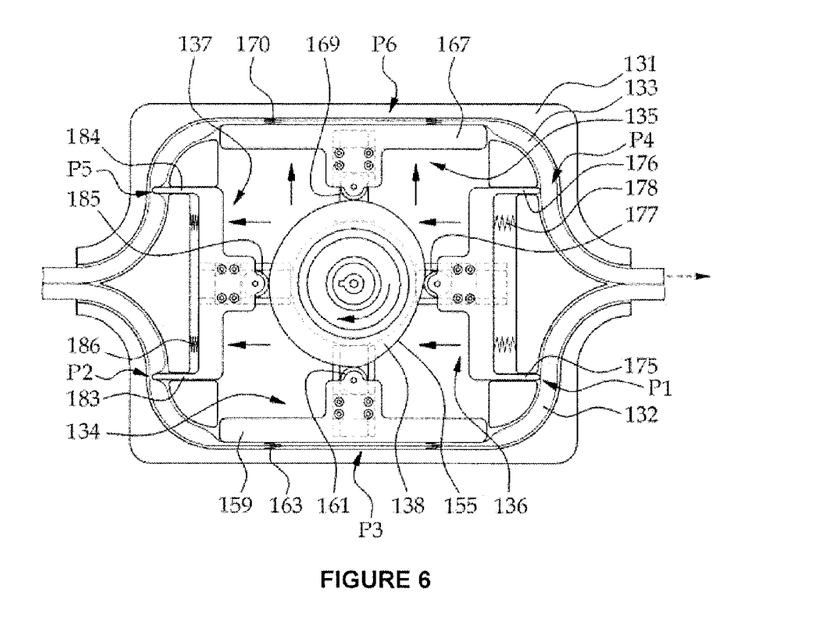

FIG. 6 illustrates a state in which the cam 138 is rotated to apply pressure to the second pumping pressure member 135 and the second backflow pressure preventer 137, and the first backflow pressure preventer 136 is released from pressure. In this case, an inner flow path of the first portion P4 of the dialysis fluid recovery tube 133 is open as the second pressure protrusion 176 is retracted toward the cam 138. The second portion P5 of the dialysis fluid recovery tube 133 is pressed by the fourth pressure protrusion 184, thus restricting the flow of dialysis fluid through an inner flow path thereof. Also, as the middle portion P6 of the dialysis fluid recovery tube 133 is pressed, the dialysis fluid is discharged from the inside of the dialysis fluid recovery tube 133 to the dialysis fluid recovery tank 122.

Figure 7:
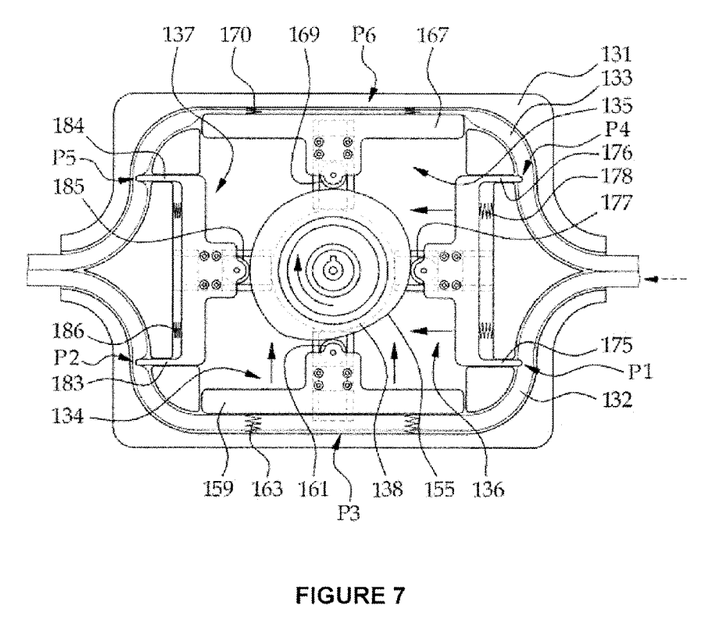

FIG. 7 illustrates a state in which the cam 138 is rotated and no longer applies pressure to the first pumping pressure member 134. In this case, the first pumping pressure member 134 is pushed toward the cam 138 by elasticity of the springs 163 and the dialysis fluid supply tube 132, and the dialysis fluid supply tube 132 expands to an original state thereof. Through this expansion of the dialysis fluid supply tube 132, the interior pressure of the dialysis fluid supply tube 132 is reduced, which causes the dialysis fluid inside the dialysis fluid supply tank 120 to be suctioned into the dialysis fluid supply tube 132. Since the second portion P2 of the dialysis fluid supply tube 132 is pressed by the third pressure protrusion 183, there occurs no backflow of dialysis fluid from the hemodialysis filter 110 to the dialysis fluid supply tube 132.

Figure 8:
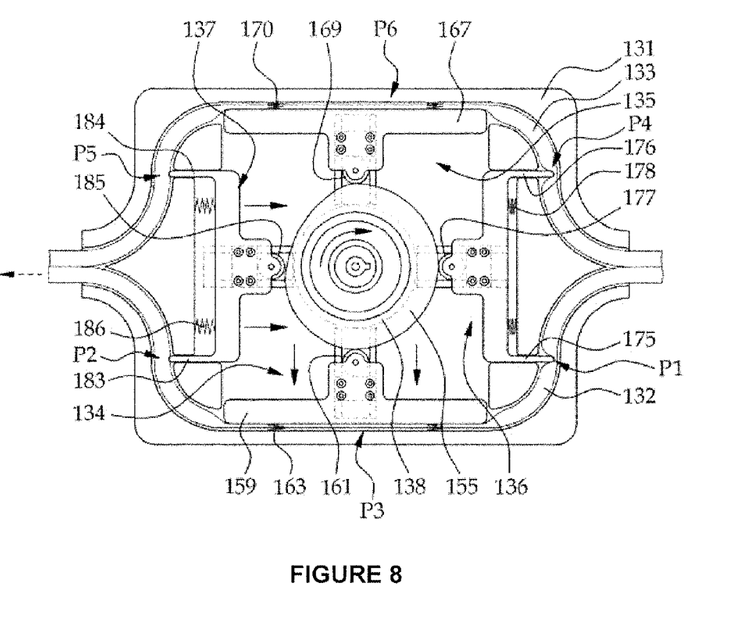

FIG. 8 illustrates a state in which the cam 138 is rotated to apply pressure to the first pumping pressure member 134 and the first backflow pressure preventer 136, and the second backflow pressure preventer 137 is released from pressure. In this case, the middle portion P3 of the dialysis fluid supply tube 132 is pressed by the first pumping pressure member 134, the first portion P1 is pressed by the first pressure protrusion 175, and an inner flow path of the second portion P2 is open as the third pressure protrusion 183 is retracted toward the cam 138. As the middle portion P3 of the dialysis fluid supply tube 132 is pressed in the state in which the first portion P1 is pressed and the inner flow path of the second portion P2 is open, the dialysis fluid is discharged from the inside of the dialysis fluid supply tube 132 to the hemodialysis filter 110.

Figure 9:
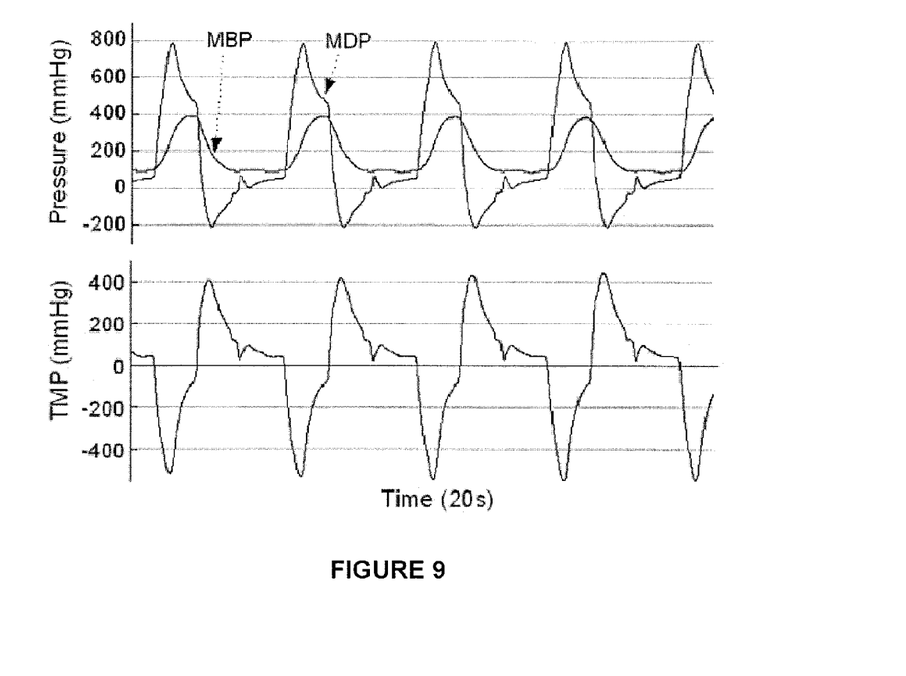
FIG. 9 is a graph illustrating mean blood pressure MBP, mean dialysate pressure MDP, and a pressure difference between the mean blood pressure and the mean dialysate pressure in the hemodialysis apparatus according to the embodiment of the present invention.

FIG. 9 illustrates mean blood pressure MBP, mean dialysate pressure MDP, and a pressure difference TMP between the mean blood pressure and the mean dialysate pressure in the hemodialysis apparatus 100 according to the embodiment of the present invention. As will be appreciated from FIG. 9, the dialysis fluid pump 130 according to the embodiment of the present invention may increase the magnitude of a pressure difference between the blood and the dialysis fluid and the frequency of the occurrence of the pressure difference by generating pulsating flow of the dialysis fluid to be supplied to the hemodialysis filter 110. In this way, enhanced hemodialysis efficiency may be accomplished.

In the present invention, the dialysis fluid supply tube 132 or the dialysis fluid recovery tube 133 may be directly pressed by the cam 138 with omission of the first pumping pressure member 134 or the second pumping pressure member 135. In this case, to prevent wear and damage to the dialysis fluid supply tube 132 or the dialysis fluid recovery tube 133 due to contact with the cam surface 155, a reinforcing member may be coupled to an outer surface of the dialysis fluid supply tube 132 or the dialysis fluid recovery tube 133 so as to come into contact with the cam surface 155. The plurality of springs 163, 170, 177 and 186, which are used to elastically push the first pumping pressure member 134, the second pumping pressure member 135, the first backflow pressure preventer 136 and the second backflow pressure preventer 137, may be replaced by various other elastic members.

The embodiment of the present invention described above and illustrated in the drawings should not be construed as limiting the technical spirit of the present invention. The scope of the present invention should be defined as disclosed in the accompanying claims, and those skilled in the art will appreciate that various modifications, additions and substitutions are possible without departing from the scope and spirit of the invention.

The invention claimed is:

1. A dialysis fluid pump for pumping dialysis fluid from a dialysis fluid supply tank to a hemodialysis filter and in turn from the hemodialysis filter to a dialysis fluid recovery tank, the dialysis fluid pump comprising:

a housing having an accommodating space therein;

a dialysis fluid supply tube formed of a flexible material that can be contracted and relaxed, wherein at least a portion of the dialysis fluid supply tube is accommodated in the accommodating space, and one end of the dialysis fluid supply tube is connected to the dialysis fluid supply tank and the other end is connected to the hemodialysis filter;

a dialysis fluid recovery tube formed of a flexible material that can be contracted and relaxed, wherein at least a portion of the dialysis fluid recovery tube is accommodated in the accommodating space, and one end of the dialysis fluid recovery tube is connected to the dialysis fluid recovery tank and the other end is connected to the hemodialysis filter;

a cam rotatably installed in the accommodating space, wherein the cam has a cam surface for pressing the dialysis fluid supply tube and the dialysis fluid recovery tube to discharge the dialysis fluid from the inside of the dialysis fluid supply tube and of the dialysis fluid recovery tube, respectively;

a motor for rotating the cam;

a first backflow pressure preventer movably installed in the accommodating space so as to be pushed by the cam, wherein the first backflow pressure preventer includes a first pressure protrusion adapted to contract a first portion of the dialysis fluid supply tube accommodated in the accommodating space so as to prevent the dialysis fluid in the dialysis fluid supply tube from flowing backward to the dialysis fluid supply tank and a second pressure protrusion adapted to contract a first portion of the dialysis fluid recovery tube accommodated in the accommodating space so as to prevent the dialysis fluid in the dialysis fluid recovery tank from flowing backward to the dialysis fluid recovery tube; and a second backflow pressure preventer movably installed in the accommodating space so as to be pushed by the cam, wherein the second backflow pressure preventer includes a third pressure protrusion adapted to contract a second portion of the dialysis fluid supply tube accommodated in the accommodating space so as to prevent the dialysis fluid in the hemodialysis filter from flowing backward to the dialysis fluid supply tube and a fourth pressure protrusion adapted to contract a second portion of the dialysis fluid recovery tube accommodated in the accommodating space so as to prevent the dialysis fluid in the dialysis fluid recovery tube from flowing backward to the hemodialysis filter.

2. The dialysis fluid pump according to claim 1, further comprising:
   a first pumping pressure member movably installed in the accommodating space so as to be pushed by the cam, wherein the first pumping pressure member includes a pressure surface adapted to press a third portion between the first portion and the second portion of the dialysis fluid supply tube so as to discharge the dialysis fluid from the inside of the dialysis fluid supply tube; and
   a second pumping pressure member movably installed in the accommodating space so as to be pushed by the cam, wherein the second pumping pressure member includes a pressure surface adapted to press a third portion between the first portion and the second portion of the dialysis fluid recovery tube so as to discharge the dialysis fluid from the inside of the dialysis fluid recovery tube.

3. The dialysis fluid pump according to claim 2, further comprising elastic members connected respectively to the first pumping pressure member, the second pumping pressure member, the first backflow pressure preventer and the second backflow pressure preventer, to elastically push the first pumping pressure member, the second pumping pressure member, the first backflow pressure preventer and the second backflow pressure preventer toward the cam.

4. The dialysis fluid pump according to claim 2, further comprising:
   first guide means for coupling the first pumping pressure member to the housing in a sliding manner, to guide linear movement of the first pumping pressure member;
   second guide means for coupling the second pumping pressure member to the housing in a sliding manner, to guide linear movement of the second pumping pressure member;
   third guide means for coupling the first backflow pressure preventer to the housing in a sliding manner, to guide linear movement of the first backflow pressure preventer; and
   fourth guide means for coupling the second backflow pressure preventer to the housing in a sliding manner, to guide linear movement of the second backflow pressure preventer.

5. The dialysis fluid pump according to claim 2, wherein the first pumping pressure member, the second pumping pressure member, the first backflow pressure preventer and the second backflow pressure preventer are arranged at an interval of 90 degrees around the cam, such that the first pumping pressure member and the second pumping pressure member face each other with the cam interposed therebetween and the first backflow pressure preventer and the second backflow pressure preventer face each other with the cam interposed therebetween.

6. The dialysis fluid pump according to claim 2, wherein a plurality of contact rollers is rotatably coupled respectively to distal ends of the first pumping pressure member, the second pumping pressure member, the first backflow pressure preventer, and the second backflow pressure preventer, so as to come into contact with the cam surface.

7. A hemodialysis apparatus comprising:
   a hemodialysis filter to permit passage of blood and dialysis fluid therethrough, wherein the hemodialysis filter includes a dialysis membrane adapted to enable mass transfer between the blood and the dialysis fluid;
   a blood pump for pumping the blood to the hemodialysis filter;
   a dialysis fluid supply tank for storing clean dialysis fluid;
   a dialysis fluid recovery tank for recovering the dialysis fluid having passed through the hemodialysis filter; and
   a dialysis fluid pump for pumping dialysis fluid from the dialysis fluid supply tank to the hemodialysis filter and in turn from the hemodialysis filter to the dialysis fluid recovery tank,
wherein the dialysis fluid pump includes:
a housing having an accommodating space therein;
a dialysis fluid supply tube formed of a flexible material that can be contracted and relaxed, wherein at least a portion of the dialysis fluid supply tube is accommodated in the accommodating space, and one end of the dialysis fluid supply tube is connected to the dialysis fluid supply tank and the other end is connected to the hemodialysis filter;
a dialysis fluid recovery tube formed of a flexible material that can be contracted and relaxed, wherein at least a portion of the dialysis fluid recovery tube is accommodated in the accommodating space, and one end of the dialysis fluid recovery tube is connected to the dialysis fluid recovery tank and the other end is connected to the hemodialysis filter;
a cam rotatably installed in the accommodating space, wherein the cam has a cam surface for pressing the dialysis fluid supply tube and the dialysis fluid recovery tube to discharge the dialysis fluid from the inside of the dialysis fluid supply tube and of the dialysis fluid recovery tube, respectively;
a motor for rotating the cam;
a first backflow pressure preventer movably installed in the accommodating space so as to be pushed by the cam, wherein the first backflow pressure preventer includes a first pressure protrusion adapted to contract a first portion of the dialysis fluid supply tube accommodated in the accommodating space so as to prevent the dialysis fluid in the dialysis fluid supply tube from flowing backward to the dialysis fluid supply tank and a second pressure protrusion adapted to contract a first portion of the dialysis fluid recovery tube accommodated in the accommodating space so as to prevent the dialysis fluid in the dialysis fluid recovery tank from flowing backward to the dialysis fluid recovery tube; and
a second backflow pressure preventer movably installed in the accommodating space so as to be pushed by the cam, wherein the second backflow pressure preventer includes a third pressure protrusion adapted to contract a second portion of the dialysis fluid supply tube accommodated in the accommodating space so as to prevent the dialysis fluid in the hemodialysis filter from flowing backward to the dialysis fluid supply tube and a fourth pressure protrusion adapted to contract a second portion of the dialysis fluid recovery tube accommodated in the accommodating space so as to prevent the dialysis fluid in the dialysis fluid recovery tube from flowing backward to the hemodialysis filter.

* * * * *